(12) United States Patent
Schmidt

(10) Patent No.: US 7,611,694 B2
(45) Date of Patent: *Nov. 3, 2009

(54) AEROSOL FORMULATION FOR INHALATION COMPRISING AN ANTICHOLINERGIC

(75) Inventor: Friedrich Schmidt, Ingelheim am Rhein (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/424,541

(22) Filed: Jun. 15, 2006

(65) Prior Publication Data

US 2006/0222598 A1    Oct. 5, 2006

Related U.S. Application Data

(63) Continuation of application No. 10/637,769, filed on Aug. 8, 2003, now abandoned.

(60) Provisional application No. 60/415,852, filed on Oct. 3, 2002.

(30) Foreign Application Priority Data

Aug. 14, 2002  (DE)  ................. 102 37 232
Aug. 31, 2002  (DE)  ................. 102 40 257

(51) Int. Cl.
*A61K 9/08*  (2006.01)
*A61K 9/12*  (2006.01)
*A61K 31/40*  (2006.01)

(52) U.S. Cl. .................. 424/45; 514/219; 514/826; 128/200.14

(58) Field of Classification Search .............. 424/45; 514/291, 826; 128/200.14
See application file for complete search history.

(56) References Cited

U.S. PATENT DOCUMENTS

| | | | |
|---|---|---|---|
| 6,150,418 A * | 11/2000 | Hochrainer et al. | ......... 514/630 |
| 6,176,442 B1 | 1/2001 | Eicher et al. | |
| 6,491,897 B1 * | 12/2002 | Freund et al. | ................ 424/45 |
| 6,706,726 B2 | 3/2004 | Meissner et al. | |
| 6,747,154 B2 | 6/2004 | Brandenburg et al. | |
| 6,890,517 B2 * | 5/2005 | Drechsel et al. | ............... 424/45 |
| 7,084,153 B2 * | 8/2006 | Banholzer et al. | ........... 514/291 |
| 7,244,742 B2 * | 7/2007 | Pieper et al. | ................ 514/291 |
| 7,273,603 B2 * | 9/2007 | Schmidt | ..................... 424/45 |
| 2003/0223937 A1 | 12/2003 | Banholzer et al. | |
| 2004/0002502 A1 | 1/2004 | Banholzer et al. | |
| 2004/0010003 A1 | 1/2004 | Banholzer et al. | |
| 2004/0024007 A1 | 2/2004 | Pairet et al. | |
| 2004/0044020 A1 | 3/2004 | Meade et al. | |
| 2004/0048886 A1 | 3/2004 | Meade et al. | |
| 2004/0048887 A1 | 3/2004 | Meade et al. | |
| 2004/0058950 A1 | 3/2004 | Meade et al. | |
| 2004/0087617 A1 | 5/2004 | Meissner et al. | |
| 2004/0228805 A1 | 11/2004 | Pieper et al. | |
| 2005/0004228 A1 | 1/2005 | Konetzki | |
| 2005/0008578 A1 | 1/2005 | Schmidt | |
| 2005/0025718 A1 | 2/2005 | Meade et al. | |
| 2005/0101625 A1 | 5/2005 | Boeck et al. | |
| 2005/0154006 A1 | 7/2005 | Meade et al. | |
| 2005/0186175 A1 | 8/2005 | Meade et al. | |
| 2005/0197357 A1 * | 9/2005 | Meissner et al. | ............ 514/291 |
| 2006/0110329 A1 * | 5/2006 | Pieper | ...................... 424/45 |
| 2006/0110330 A1 * | 5/2006 | Pieper | ...................... 424/45 |

FOREIGN PATENT DOCUMENTS

| | | |
|---|---|---|
| CA | 2 105 575 C1 | 9/1992 |
| WO | WO 91/14468 | 10/1991 |
| WO | 9407607 A1 | 4/1994 |
| WO | WO 97/12687 | 4/1997 |
| WO | 9720590 A1 | 6/1997 |
| WO | 9916530 A1 | 4/1999 |
| WO | WO 01/89480 | 11/2001 |

* cited by examiner

*Primary Examiner*—Mina Haghighatian
(74) *Attorney, Agent, or Firm*—Michael P. Morris; Mary-Ellen M. Devlin; Wendy A. Petka

(57) ABSTRACT

The present invention relates to a propellant-free, aqueous aerosol formulation for anticholinergics of formula 1 wherein $X^-$ denotes an anion.

11 Claims, No Drawings

AEROSOL FORMULATION FOR INHALATION COMPRISING AN ANTICHOLINERGIC

This application is a continuation of U.S. patent application Ser. No. 10/637,769 filed on Aug. 8, 2003, which claims benefit under 35 U.S.C. 119(e) of U.S. Provisional Patent Application No. 60/415,852 filed on Oct. 3, 2002. These applications are incorporated herein by reference in their entirety.

The present invention relates to a propellant-free aqueous aerosol formulation for anticholinergics of formula 1 wherein $X^-$ denotes an anion.

The compounds of formula 1 are known from WO 02/32899. They have valuable pharmacological properties and can provide therapeutic benefit as highly effective anticholinergics in the treatment of respiratory complaints, particularly in the treatment of inflammatory and/or obstructive diseases of the respiratory tract, particularly for treating asthma or COPD (chronic obstructive pulmonary disease).

The present invention relates to liquid active substance formulations of these compounds which can be administered by inhalation; the liquid formulations according to the invention have to meet high quality standards. The formulations according to the invention may be inhaled by oral or nasal route. To achieve an optimum distribution of the active substances in the lung, it makes sense to use a liquid formulation without propellant gases and to administer by using suitable inhalers. A formulation of this kind may be inhaled both by oral route and by nasal route. Those inhalers which are capable of nebulising a small amount of a liquid formulation in the dosage needed for therapeutic purposes within a few seconds into an aerosol suitable for therapeutic inhalation are particularly suitable. Within the scope of the invention, preferred nebulisers are those in which an amount of less than 100 microliters, preferably less than 50 microliters, most preferably less than 20 microliters of active substance solution can be nebulised preferably in one puff or two puffs, to form an aerosol having an average particle size of less than 20 microns, preferably less than 10 microns, so that the inhalable part of the aerosol already corresponds to the therapeutically effective quantity.

An apparatus of this kind for the propellant-free administration of a metered amount of a liquid pharmaceutical composition for inhalation is described in detail in, for example International Patent Application WO 91/14468, "Atomizing Device and Methods" and also in WO 97/12687, cf. FIGS. 6a and 6b and the accompanying description. In a nebuliser of this kind, a pharmaceutical solution is converted by means of a high pressure (up to 500 bar) into an aerosol destined for the lungs. The aerosol is then sprayed. Within the scope of the present specification reference is expressly made to the entire contents of the literature mentioned above.

In inhalers of this kind, the formulations of solutions are stored in a reservoir. It is essential that the active substance formulations used are sufficiently stable when stored and at the same time are such that they can be administered directly, if possible without any further handling, in accordance with their medical purpose. Moreover, they must not contain any ingredients which might interact with the inhaler in such a way as to damage the inhaler or the pharmaceutical quality of the solution or of the aerosol produced.

To nebulise the solution, a special nozzle is used as described, for example, in WO 94/07607 or WO 99/16530. Reference is expressly made here to both these publications.

The aim of the invention is to provide an aqueous formulation of the compound of formula 1 which meets the high standards required to ensure optimum nebulisation of a solution using the inhalers mentioned above. The active substance formulations according to the invention must be of sufficiently high pharmaceutical quality, i.e., they should be pharmaceutically stable over a storage time of some years, preferably at least one year, more preferably two years. These propellant-free formulations of solutions must also be capable of being nebulised by means of an inhaler under pressure, while the composition delivered in the aerosol produced is within a specified range.

Within the scope of the present invention, the compounds of formula 1 are preferably used wherein the anion $X^-$ is selected from among the chloride, bromide, iodide, sulphate, phosphate, methanesulphonate, nitrate, maleate, acetate, citrate, fumarate, tartrate, oxalate, succinate, benzoate and p-toluenesulphonate.

Preferably, the salts of formula 1 are used wherein $X^-$ denotes an anion selected from the group consisting of chloride, bromide, 4-toluenesulphonate and methanesulphonate.

Particularly preferred, within the scope of the present invention, are the formulations which contain the compound of formula 1 wherein $X^-$ denotes bromide.

References to the compound of formula 1 always include within the scope of the present invention all possible amorphous and crystalline modifications of this compound. References to the compound of formula 1 also include within the scope of the present invention all the possible solvates and hydrates which may be formed from this compound.

Any reference to the compound 1' within the scope of the present invention is to be regarded as a reference to the pharmacologically active cation of the following formula contained in the salts 1.

In the formulation according to the invention, the compound 1 is present dissolved in water. If desired, cosolvents may be used. Preferably, according to the invention, no other solvent is used.

According to the invention, the formulation preferably contains only a single salt of formula 1. However, the formulation may also contain a mixture of different salts of formula 1. Formulations which contain active substances other than those of formula 1 are not an object of the invention.

The concentration of the compound of formula 1 based on the proportion of pharmacologically active cation 1' in the pharmaceutical preparation according to the invention is about 4 to 2000 mg per 100 ml, according to the invention, preferably about 8 to 1600 mg per 100 ml. Particularly preferably, 100 ml of the formulations according to the invention contain about 80 to about 1360 mg of 1'.

If the compound of formula 1 used is the particularly preferred compound wherein $X^-$ denotes the bromide, the proportion of 1 according to the invention is about 5 to 2500 mg per 100 ml, preferably about 10 to 2000 mg per 100 ml of pharmaceutical preparation. Most preferably, 100 ml of the formulations according to the invention contain about 100 to 1700 mg of 1.

The pH of the formulation according to the invention is preferably between 2.5 and 6.5 and more preferably between 3.0 and 5.0, more preferably between about 3.5 and 4.5.

The pH is adjusted by the addition of pharmacologically acceptable acids. Pharmacologically acceptable inorganic acids or organic acids may be used for this purpose. Examples of preferred inorganic acids are selected from the group consisting of hydrochloric acid, hydrobromic acid, nitric acid, sulphuric acid and phosphoric acid. Examples of particularly suitable organic acids are selected from the group consisting of ascorbic acid, citric acid, malic acid, tartaric acid, maleic acid, succinic acid, fumaric acid, acetic acid, formic acid and propionic acid. Preferred inorganic acids are hydrochloric acid and sulphuric acid, of which hydrochloric acid is particularly preferred according to the invention. Of the organic acids, ascorbic acid, fumaric acid and citric acid are preferred. If desired, mixtures of the abovementioned acids may also be used, particularly in the case of acids which have other properties in addition to their acidifying properties, e.g. those which act as flavourings or antioxidants, such as for example citric acid or ascorbic acid.

If desired, pharmacologically acceptable bases may be used to titrate the pH precisely. Suitable bases include for example alkali metal hydroxides and alkali metal carbonates. The preferred alkali metal ion is sodium. If bases of this kind are used, care must be taken to ensure that the resulting salts, which are then contained in the finished pharmaceutical formulation, are pharmacologically compatible with the abovementioned acid.

The formulations according to the invention may contain complexing agents as other ingredients. By complexing agents are meant within the scope of the present invention molecules which are capable of entering into complex bonds. Preferably, these compounds should have the effect of complexing cations, most preferably metal cations. The formulations according to the invention preferably contain editic acid (EDTA) or one of the known salts thereof, e.g. sodium EDTA or disodium EDTA dihydrate (sodium edetate), as complexing agent. Preferably, sodium edetate is used, optionally in the form of its hydrates, more preferably in the form of its dihydrate. If complexing agents are used within the formulations according to the invention, their content is preferably in the range from 5 to 20 mg per 100 ml, more preferably in the range from 7 to 15 mg per 100 ml of the formulation according to the invention. Preferably, the formulations according to the invention contain a complexing agent in an amount of about 9 to 12 mg per 100 ml, more preferably about 10 mg per 100 ml of the formulation according to the invention.

The remarks made concerning sodium edetate also apply analogously to other possible additives which are comparable to EDTA or the salts thereof, which have complexing properties and can be used instead of them, such as for example nitrilotriacetic acid and the salts thereof.

Other pharmacologically acceptable excipients may also be added to the formulation according to the invention. By adjuvants and additives are meant, in this context, any pharmacologically acceptable and therapeutically useful substance which is not an active substance, but can be formulated together with the active substance in the pharmacologically suitable solvent, in order to improve the qualities of the active substance formulation. Preferably, these substances have no pharmacological effects or no appreciable or at least no undesirable pharmacological effects in the context of the desired therapy. The adjuvants and additives include, for example, stabilisers, antioxidants and/or preservatives which prolong the shelf life of the finished pharmaceutical formulation, as well as flavourings, vitamins and/or other additives known in the art. The additives also include pharmacologically acceptable salts such as sodium chloride, for example.

The preferred excipients include antioxidants such as ascorbic acid, for example, provided that it has not already been used to adjust the pH, vitamin A, vitamin E, tocopherols and similar vitamins or provitamins occurring in the human body.

Preservatives can be added to protect the formulation from contamination with pathogenic bacteria. Suitable preservatives are those known from the prior art, particularly benzalkonium chloride or benzoic acid or benzoates such as sodium benzoate in the concentration known from the prior art. Preferably, benzalkonium chloride is added to the formulation according to the invention. The amount of benzalkonium chloride is between 1 mg and 50 mg per 100 ml of formulation, preferably about 7 to 15 mg per 100 ml, more preferably about 9 to 12 mg per 100 ml of the formulation according to the invention.

Preferred formulations contain only benzalkonium chloride, sodium edetate and the acid needed to adjust the pH, preferably hydrochloric acid, in addition to the solvent water and the compounds of formula 1.

The pharmaceutical formulations according to the invention containing compounds of formula 1 are preferably used in an inhaler of the kind described hereinbefore in order to produce the propellant-free aerosols according to the invention. At this point, we should once again expressly mention the patent documents described hereinbefore, to which reference is hereby made.

As described at the beginning, a further developed embodiment of the preferred inhaler is disclosed in WO 97/12687 (cf. in particular FIGS. 6a and 6b and the associated passages of description). This nebuliser (known under the trademark Respimat®) can advantageously be used to produce the inhalable aerosols according to the invention containing a tiotropium salt as active substance. Because of its cylindrical shape and handy size of less than 9 to 15 cm long and 2 to 4 cm wide, the device can be carried anywhere by the patient. The nebuliser sprays a defined volume of the pharmaceutical formulation out through small nozzles at high pressures, so as to produce inhalable aerosols.

The preferred atomiser essentially consists of an upper housing part, a pump housing, a nozzle, a locking clamp, a spring housing, a spring and a storage container, characterised by a pump housing fixed in the upper housing part and carrying at one end a nozzle body with the nozzle or nozzle arrangement, a hollow piston with valve body, a power take-off flange in which the hollow body is fixed and which is located in the upper housing part, a locking clamping mechanism located in the upper housing part, a spring housing with the spring located therein, which is rotatably mounted on the upper housing part by means of a rotary bearing, a lower housing part which is fitted onto the spring housing in the axial direction.

The hollow piston with valve body corresponds to a device disclosed in WO 97/12687. It projects partially into the cylinder of the pump housing and is disposed to be axially movable in the cylinder. Reference is made particularly to FIGS. 1-4—especially FIG. 3—and the associated passages of description in the abovementioned International Patent Application. At the moment of release of the spring, the hollow piston with valve body exerts, at its high pressure end, a pressure of 5 to 60 Mpa (about 50 to 600 bar), preferably 10 to 60 Mpa (about 100 to 600 bar) on the fluid, which is a measured amount of active substance solution. Volumes of 10 to 50 microliters are preferred, volumes of 10 to 20 microliters are more preferable, whilst a volume of 10 to 15 microliters per actuation is particularly preferred.

The valve body is preferably mounted at the end of the hollow piston which faces the nozzle body.

The nozzle in the nozzle body is preferably microstructured, i.e., produced by micro-engineering. Microstructured nozzle bodies are disclosed for example in WO-99/16530; reference is hereby made to the contents of this specification, especially FIG. 1 and the associated description.

The nozzle body consists for example of two sheets of glass and/or silicon securely fixed together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns and the length being 7 to 9 microns.

If there is a plurality of nozzle openings, preferably two, the directions of spraying of the nozzles in the nozzle body may run parallel to each other or may be inclined relative to one another in the direction of the nozzle opening. In the case of a nozzle body having at least two nozzle openings at the outlet end, the directions of spraying may be inclined relative to one another at an angle of 20 degrees to 160 degrees, preferably at an angle of 60 to 150 degrees, most preferably 80 to 100°. The nozzle openings are preferably arranged at a spacing of 10 to 200 microns, more preferably at a spacing of 10 to 100 microns, still more preferably 30 to 70 microns. A spacing of 50 microns is most preferred.

The directions of spraying therefore meet in the region of the nozzle openings.

As already mentioned, the liquid pharmaceutical preparation hits the nozzle body at an entry pressure of up to 600 bar, preferably 200 to 300 bar and is atomised through the nozzle openings into an inhalable aerosol. The preferred particle sizes of the aerosol are up to 20 microns, preferably 3 to 10 microns.

The locking clamping mechanism contains a spring, preferably a cylindrical helical compression spring, as a store for the mechanical energy. The spring acts on the power take-off flange as a spring member, the movement of which is determined by the position of a locking member. The travel of the power take-off flange is precisely limited by an upper stop and a lower stop. The spring is preferably tensioned via a stepping-up gear, e.g., a helical sliding gear, by an external torque which is generated when the upper housing part is turned relative to the spring housing in the lower housing part. In this case, the upper housing part and the power take-off flange contain a single- or multi-speed spline gear.

The locking member with the engaging locking surfaces is arranged in an annular configuration around the power take-off flange. It consists, for example, of a ring of plastics or metal which is inherently radially elastically deformable. The ring is arranged in a plane perpendicular to the axis of the atomiser. After locking of the spring, the locking surfaces of the locking member slide into the path of the power take-off flange and prevent the spring from being released. The locking member is actuated by means of a button. The actuating button is connected or coupled to the locking member. In order to actuate the locking clamping mechanism, the actuating button is moved parallel to the annular plane, preferably into the atomiser, and the deformable ring is thereby deformed in the annular plane. Details of the construction of the locking clamping mechanism are described in WO 97/20590.

The lower housing part is pushed axially over the spring housing and covers the bearing, the drive for the spindle and the storage container for the fluid.

When the atomiser is operated, the upper part of the housing is rotated relative to the lower part, the lower part taking the spring housing with it. The spring meanwhile is compressed and biased by means of the helical sliding gear, and the clamping mechanism engages automatically. The angle of rotation is preferably a whole-number fraction of 360 degrees, e.g., 180 degrees. At the same time that the spring is tensioned, the power take-off component in the upper housing part is moved along by a given amount, the hollow piston is pulled back inside the cylinder in the pump housing, as a result of which some of the fluid from the storage container is sucked into the high pressure chamber in front of the nozzle.

If desired, a plurality of replaceable storage containers containing the fluid to be atomised can be inserted in the atomiser one after another and then used. The storage container contains the aqueous aerosol preparation according to the invention.

The atomising process is initiated by gently pressing the actuating button. The clamping mechanism then opens the way for the power take-off component. The biased spring pushes the piston into the cylinder in the pump housing. The fluid emerges from the nozzle of the atomiser in the form of a spray.

Further details of the construction are disclosed in PCT applications WO 97/12683 and WO 97/20590, to which reference is hereby made.

The components of the atomiser (nebuliser) are made of a material suitable for their function. The housing of the atomiser and—if the function allows—other parts as well are preferably made of plastics, e.g., by injection moulding. For medical applications, physiologically acceptable materials are used.

FIGS. 6*a/b* of WO 97/12687 show the Respimat® nebuliser with which the aqueous aerosol preparations according to the invention can advantageously be inhaled.

FIG. 6*a* shows a longitudinal section through the atomiser with the spring under tension, FIG. 6*b* shows a longitudinal section through the atomiser with the spring released.

Referencing those drawings, the upper housing part (51) contains the pump housing (52), on the end of which is mounted the holder (53) for the atomiser nozzle. In the holder is the nozzle body (54) and a filter (55). The hollow piston (57) fixed in the power take-off flange (56) of the locking clamping mechanism projects partly into the cylinder of the pump housing. At its end the hollow piston carries the valve body (58). The hollow piston is sealed off by the gasket (59). Inside the upper housing part is the stop (60) on which the power take-off flange rests when the spring is relaxed. Located on the power take-off flange is the stop (61) on which the power take-off flange rests when the spring is under tension. After the tensioning of the spring, the locking member (62) slides between the stop (61) and a support (63) in the upper housing part. The actuating button (64) is connected to the locking member. The upper housing part ends in the mouthpiece (65) and is closed off by the removable protective cap (66).

The spring housing (67) with compression spring (68) is rotatably mounted on the upper housing part by means of the snap-fit lugs (69) and rotary bearings. The lower housing part (70) is pushed over the spring housing. Inside the spring housing is the replaceable storage container (71) for the fluid (72) which is to be atomised. The storage container is closed off by the stopper (73), through which the hollow piston projects into the storage container and dips its end into the fluid (supply of active substance solution).

The spindle (74) for the mechanical counter is mounted on the outside of the spring housing. The drive pinion (75) is located at the end of the spindle facing the upper housing part. On the spindle is the slider (76).

The nebuliser described above is suitable for nebulising the aerosol preparations according to the invention to form an aerosol suitable for inhalation.

If the formulation according to the invention is nebulised using the method described above (that is, by use of the Respimat® device), the mass expelled, in at least 97%, preferably at least 98% of all the actuations of the inhaler (puffs) should correspond to a defined quantity with a range of tolerance of not more than 25%, preferably 20%, of this quantity. Preferably, between 5 and 30 mg, and more preferably between 5 and 20 mg, of formulation are delivered as a defined mass per puff.

However, the formulation according to the invention can also be nebulised using inhalers other than those described above, for example, using jet-stream inhalers.

The present invention also relates to an inhalation kit consisting of one of the pharmaceutical preparations according to the invention described above, and an inhaler suitable for nebulising this pharmaceutical preparation. The present invention preferably relates to an inhalation kit consisting of one of the pharmaceutical preparations according to the invention described above and the Respimat® inhaler described above.

The examples of formulations given below serve as illustrations without restricting the subject matter of the present invention to the compositions shown by way of example.

I. EXAMPLES OF FORMULATIONS 100 ml of pharmaceutical preparation contain, in purified water or water for injections, with a density of 1.00 g/cm³, at a temperature of 15° C. to 31° C.:

| Example | 1 (1'-Bromide) (mg) | Benzalkonium chloride (mg) | Disodium edetate dihydrate (mg) | Citric acid (mg) |
| --- | --- | --- | --- | --- |
| 1 | 2000 | 10 | 10 | 3 |
| 2 | 1000 | 9 | 9 | 3 |
| 3 | 1500 | 12 | 12 | 5 |
| 4 | 500 | 10 | 12 | 2 |
| 5 | 150 | 7 | 12 | 3 |
| 6 | 250 | 15 | 7 | 2 |
| 7 | 750 | 12 | 15 | 4 |
| 8 | 150 | — | 12 | 3 |
| 9 | 250 | — | 7 | 4 |
| 10 | 750 | — | 15 | 3 |
| 11 | 100 | 5 | 10 | 3 |

What is claimed is:

1. An propellant-free aqueous pharmaceutical formulation for inhalation comprising at least one compound of formula 1 as the only active substance wherein
   X⁻ is an anion selected from the group consisting of chloride, bromide, iodide, sulphate, phosphate, methanesulphonate, nitrate, maleate, acetate, citrate, fumarate, tartrate, oxalate, succinate, benzoate and p-toluenesulphonate,
   at least one pharmacologically acceptable acid and water, which formulation is a liquid.

2. The propellant-free aqueous pharmaceutical formulation according to claim 1 further comprising one or more pharmaceutically acceptable excipients or complexing agents or mixtures thereof.

3. The propellant-free aqueous pharmaceutical formulation according to claim 1, containing at least one compound of formula 1 wherein X⁻ is selected from the group consisting of chloride, bromide, 4-toluenesulphonate and methanesulphonate.

4. The propellant-free aqueous pharmaceutical formulation according to claim 1, wherein the pharmacologically acceptable acid is selected from the inorganic acids hydrochloric acid, hydrobromic acid, nitric acid, sulphuric acid and phosphoric acid or from the organic acids ascorbic acid, citric acid, malic acid, tartaric acid, maleic acid, succinic acid, fumaric acid, acetic acid, formic acid and propionic acid.

5. The propellant-free aqueous pharmaceutical formulation according to claim 3, characterised by a pH of 2.5 to 6.5.

6. The propellant-free aqueous pharmaceutical formulation according to claim 2, wherein the pharmaceutical excipient is benzalkonium chloride.

7. The propellant-free aqueous pharmaceutical formulation according to claim 6, characterised in that the content of benzalkonium chloride is from 1 to 50 mg per 100 ml of solution.

8. The propellant-free aqueous pharmaceutical formulation according to claim 1, characterised in that a pharmacologically active cation of the compound of 1 is present in the formulation in an amount of about 4 to 2000 mg per 100 ml of formulation.

9. The propellant-free aqueous pharmaceutical formulation according to claim 2, which comprises at least one complexing agent.

10. The propellant-free aqueous pharmaceutical formulation according to claim 9, characterised in that the content of the complexing agent is 5 to 20 mg per 100 ml of formulation.

11. The propellant-free aqueous pharmaceutical formulation according to claim 1 in an inhaler suitable for nebulising the formulation.

* * * * *